United States Patent [19]
Futatsugi et al.

[11] Patent Number: 5,879,901
[45] Date of Patent: Mar. 9, 1999

[54] REAGENT AND METHODS FOR MEASURING LDL-CHOLESTEROL

[75] Inventors: Masayuki Futatsugi; Ikuko Tanaka, both of Amagasaki, Japan

[73] Assignee: Wako Pure Chemical Industries, Ltd., Osaka, Japan

[21] Appl. No.: 895,879

[22] Filed: Jul. 17, 1997

[30] Foreign Application Priority Data

Jul. 18, 1996 [JP] Japan .................................. 8-207770

[51] Int. Cl.$^6$ ...................................................... C12Q 1/60
[52] U.S. Cl. ................................ 435/11; 435/19; 435/962
[58] Field of Search .................................. 435/11, 19, 25, 435/28, 962; 436/13, 71; 422/56

[56] References Cited

U.S. PATENT DOCUMENTS

| | | | |
|---|---|---|---|
| 4,892,815 | 1/1990 | Kerscher et al. | 435/7 |
| 5,286,626 | 2/1994 | Law et al. | 435/19 |
| 5,411,870 | 5/1995 | Law et al. | 435/11 |
| 5,691,154 | 11/1997 | Callstrom et al. | 435/7.6 |

FOREIGN PATENT DOCUMENTS

| | | |
|---|---|---|
| 7-163339 | 6/1995 | Japan . |
| 8-187095 | 7/1996 | Japan . |

*Primary Examiner*—Ralph Gitomer
*Attorney, Agent, or Firm*—Armstrong, Westerman, Hattori, McLeland & Naughton

[57] ABSTRACT

The present invention provides a method for measuring an amount of LDL-cholesterol in samples specifically and accurately and also a reagent used for the method, and by using the present invention, such effect can be attained that LDL-cholesterol can be measured directly using so far widely used automatic analyzer, which has been impossible in known measurement methods.

12 Claims, 4 Drawing Sheets

REAGENT AND METHODS FOR MEASURING LDL-CHOLESTEROL

BACKGROUND OF INVENTION

The present invention relates to a method for measuring an amount of cholesterol in low density lipoproteins (LDL), which has been used for important factor for diagnosis of arteriosclerosis, disorder of lipid metabolism, etc. in the field of clinical chemistry test and also to a reagent used in this method.

Lipids in serum exist as lipoproteins and they are classified according to their density into chylomicrons, very low density lipoproteins (VLDL), LDL and high density lipoproteins (HDL). They are particles comprising proteins covalently bound to lipids and have a micelle-like spherical structure composed of a non-polar core consisting of triacylglycerol and cholesterol ester on one hand and proteins, cholesterol and phospholipid covering the core on the other hand, and apoproteins and lipids are different according to each lipoprotein. LDL has a particle size of about 180 to 280 angstroms in diameter and specific gravity of a range of 1.006 to 1.063 (g/ml) and its apoprotein is composed mainly of apoB-100, and 80% thereof is occupied by lipid which contains a large amount of cholesterol. On the other hand, HDL is the smallest lipoprotein having a particle size of about 50 to 120 angstroms in a diameter and such higher specific gravity as 1.063 to 1.125 (g/ml), which is enriched with proteins (mainly apoA, about 50% thereof) containing lipid composed of mainly phospholipid and cholesterol. LDL has a role of transporting cholesterol synthesized in liver to peripheral cells and HDL has, on the other hand, a role of transporting it from peripheral tissues to liver.

Among those lipoproteins, LDL has an action causing atherosclerosis which is most frequently found among arteriosclerosis (progressive disease caused by sedimentation of lipids in cells of smooth muscles in inner walls of arteries, particularly of coronary arteries), and thus an amount of cholesterol originated therefrom (LDL-cholesterol) has been remarked as a risk factor of arteriosclerosis.

However, there has been found no method for measuring LDL-cholesterol accurately after a simple procedure.

For instance, LDL-cholesterol amount obtained by the following equation proposed by Friedewald, etc. has been said as containing about 10% error;

LDL-cholesterol amount=total cholesterol amount−HDL-cholesterol amount−⅕×triglyceride amount (note: amounts are shown in mg/dl)

For this reason, using of the values obtained by this method are accompanied with such defects that (1) it is dangerous to decide as effective when an administration of medicine or diet causes 10 to 15% reduction of LDL-cholesterol amount on the basis of the value of this method, and (2) use of the value in diagnosis of coronary arteriosclerosis causes erroneous diagnosis at high probability. Further among other measurement methods, an ultracentrifugation method which has been used from a middle of 1950, for instance, is accompanied with such defects that handling is troublesome, much work and cost are necessary, skill is required for conducting the method, only a few kind of samples can be treated in one batch, a large amount of sample is required for the test, further an electrophoresis method is also accompanied with such defect that long time and cost are required for the test, accurate quantitative analysis is rather doubtful because amounts of dyes for staining are different according to the kinds of lipoproteins, etc.

SUMMARY OF THE INVENTION

The present invention has been completed under the circumstances mentioned above and the problem to be solved by the present invention is to provide a method and a reagent for directly measuring an amount of LDL-cholesterol after a simple procedure at high accuracy by using conventional automatic analyzers.

The present invention has the purpose of solving the above problems and relates to a reagent for measuring an amount of cholesterol in low density lipoproteins, which comprises a cholesterol esterase and a cholesterol oxidase, at least one of the cholesterol esterase and the cholesterol oxidase being a modified one in which the cholesterol esterase or the cholesterol oxidase binds to a sugar compound.

Further, the present invention relates to a method for measuring an amount of cholesterol in low density lipoproteins comprising using a cholesterol esterase and a cholesterol oxidase, which is characterized in that at least one of the cholesterol esterase and the cholesterol oxidase are a modified one in which the cholesterol esterase or the cholesterol oxidase binds to a sugar compound.

Further more, the present invention relates to a method for measuring an amount of cholesterol in low density lipoproteins of a living sample, which comprises mixing the living sample with a first reagent solution containing a buffering agent, measuring an absorbance (OD1) of a resulting reaction solution, mixing the resulting solution with a second reagent solution containing a cholesterol esterase and a cholesterol oxidase, measuring an absorbance (OD2) of the latter resulting solution, subtracting a value obtained by multiplying OD1 with a correction coefficient from the OD2 to give OD3, applying thus obtained OD3 a calibration curve showing a relation between an amount of cholesterol and OD3 which is previously prepared by conducting the above process with the use of a standard solution containing a predetermined amount of cholesterol, wherein at least one of the cholesterol esterase and the cholesterol oxidase are a modified one in which the enzyme binds to a sugar compound and each of the coupler and the developer is incorporated in at least one of the first reagent and the second reagent.

Namely, the present inventors have extensively studied to make function of enzyme change by modifying it chemically, and as a result of the study, the present inventors have found that a modified enzyme obtained by modifying an amino group or a carboxyl group of the cholesterol esterase and/or the cholesterol oxidase with a sugar compound has such characteristics that it does not react with cholesterol in HDL (HDL-cholesterol) and reacts specifically only with LDL-cholesterol and have continued to study on the basis of this finding to reach the present invention.

DESCRIPTION OF THE PREFERRED EMBODIMENT

The cholesterol oxidase in the present invention is not specifically limited by its origin and all of those which have so far been used in this field such as one originated from microorganisms belonging to genus Nocardia, genus Pseudomonas, etc. and one originated from animal organs such as bovine pancreas can be used.

The cholesterol esterase in the present invention is not specifically limited by its origin and all of those which have so far been used in this field such as one originated from microorganisms belonging to genus Candida, genus Pseudomonas, etc. and one originated from animal organs such as bovine pancreas can be used.

A sugar compound to be used for binding to the cholesterol esterase or the cholesterol oxidase in the present invention includes a monosaccharide such as glucose, mannose, fructose, galactose, fucose, sorbitol, allose, xylose, arinose, lyxoso, ribose, talose, gulose, idose and altrose, a disaccharide such as saccharose, mannose, lactose, maltose, isomaltose, turanose, gentiobiose, mellbiose, planteobiose, primeverose, vicianose, nigerose, laminaribiose, trehalose, rutinose, cellobiose and xylobiose, a trisaccharide such as maltotriose, raffinose, gentianose, melezitose, planteose and ketose, a water soluble polysaccharide such as amylose, dextran, pullulan, dextrin, starch and ficol, and a cyclic oligosaccharide such as alpha-cyclodextrin, beta-cyclodextrin and gamma-cyclodextrin. The molecular weight of the water soluble polysaccharide is not specifically limited and any of commercially available ones can be used and generally one having a molecular weight of 1000 to 2000000, preferably 10000 to 500000 is exemplified. The sugar compound may be those a part of whose hydroxy groups is modified. The modified sugar compounds are exemplified by those having an acid residue such as sulfuric acid residue and phosphoric acid residue, a carboxylalkyl group such as a carboxymethyl group, an amino group, a thiol group, an acyl group such as an acetoxy group, an alkyl group such as a methyl group and an ethyl group, an alkoxy group such as a methoxy group and an ethoxy group, a hydroxyalkyl group such as a hydroxymethyl group and a hydroxyethyl group, etc., and more specifically glucosamine, dextran sulfuric acid, pectic acid, alginic acid, heparin, heparan sulfuric acid, chondroitin, glycol chitin, carboxymethyl chitin, dermatanic acid, carboxymethyl cellulose, carboxymethyl dextran, alpha-, beta- or gamma-methylated cyclodextrin, alpha- , beta- or gamma-hydroxymethylated cyclodextrin, alpha- beta- or gamma-acetoxylated cyclodextrin and alpha-, beta- or gamma-cyclodextrin sulfate.

Among the above sugar compounds, those originaly containing an active group reactive to animo group(s) of an enzyme such as an amino group, an imino group, a carboxyl group, an aldehyde group, a cyanuryl group and an epichlorohydryl group (hereinafter abbreviated as the active group) can be directly subjected to the binding reaction with the cholesterol esterase or the cholesterol oxidase.

The sugar compound having no active group is used after conversion to an active form by a method for introducing the active group to the sugar compound. In the method for introducing the active group(s), the active group(s) may be bound to the sugar compound through a spacer such as an alkylene chain having 1 to 6 carbon atoms.

A method for introducing the active group may be any of those which have widely been used in this field. Typical examples of those methods are a method for introducing a cyanuryl group by cyanuryl chloride (e.g. J. Solid-phase Biochem., vol. 4, 2128, 1976), a method for introducing an aldehyde group by metaperiodic acid (e.g. Proc. Nati. Acad. Sci. U.S. A., vol. 73, 2128, 1976), a method for introducing a imino group by cyanogen bromide (e.g. Nature, vol. 214, 1302, 1967), a method for introducing a epichlorohydryl group by epichlorohydrin (e.g. J. Chromatog., vol. 51, 479, 1970), a method for introducing a carboxyl group by an acid anhydride (e.g. Japanese Patent Publication- Kokai- No. 268950/1993), a method for introducing a carboxyl group by monobromocarboxylic acid (e.g. Arc. Biochem. Biophys., vol.147, 788, 1971) and etc. A suitable method can be selected from those mentioned above in accordance with the kind of the sugar compound and properties of the cholesterol esterase or the cholesterol oxidase to be used.

In order to increase the reactivity to an enzyme, a sugar compound originaly containing the active group(s) may be at first subjected to a method for introducing the active group mentioned above, so that additional active group(s) are introduced.

In a case where the sugar compound is at first subjected to the method mentioned above and then reacted with the cholesterol esterase or the cholesterol oxidase, the resulting solution containing the sugar compound, to which the active group was introduced, may be put into use after desalting, adjustment of pH and adjustment of the kind of ions by dialysis, etc.

The sugar compound containing the active group(s) is easily covalently bound to cholesterol esterase or the cholesterol oxidase by contacting the both with each other after known methods mentioned below. Addtionaly, the sugar compound may be at first bound to a compound which can act as a ligand such as a succinidyl group for binding to an enzyme before the reaction with an enzyme.

The followings are typical examples of the above known methods.

In a case where the reactive groups participating in the covalent binding reaction are an amino group and a carboxyl group, a carbodiimide method (e.g. J. Biol. Chem., vol. 245, 3059, 1970), an active esterification method (e.g. Cancer Biochem., vol. 7, 175, 1984), an acid anhydride method (e.g. J. Biol.Chem., vol. 237, 1825, 1962), an azide method (e.g. Eur. J. Biochem., vol. 25, 129, 1972), a carboxy chloride method (e.g. Angew. Chem., vol. 67, 661, 1955), an isocyanate method (e.g. Nature, vol. 210, 367, 1966), a Woodward reagent method (e.g. Biochim. Biophys. Acta., vol. 178, 626, 1969), an Ugi reaction (e.g. Angew. Chem., vol. 74, 9, 1962), etc. are exemplified.

In a case where the reactive groups participating in the covalent binding reaction are both amino groups, a glutaraldehyde method (e.g. Experientia, vol. 28, 958, 1973), an alkylation method (e.g. Biochem. Biophys. Acta., vol. 198, 276, 1970), and in a case where the reactive groups participating in the covalent binding reaction are a hydroxy group and an amino group, an alkylation method (e.g. Biochem. Biophys. Acta., vol. 198, 276, 1970), etc. is exemplified.

In a case where the reactive groups participating in the covalent binding reaction are an amino group and an aldehyde group, a periodate oxidation method (e.g. Proc. Natl.

Acad. Sci. USA, vol. 73, 2128, 1976), etc. is exemplified and in a case where the reactive groups participating in the covalent binding reaction are an amino group and an imino group, a cyanogen bromide method (e.g. Nature, vol. 214, 1302, 1967) etc. is exemplified.

Among these methods, a method in which amino group(s) of the enzyme, especially amino group(s) of Lysine residue located at the surface of the enzyme is covalently bound to the active group(s) such as carboxyl group (s), amino group(s), imino group(s) or aldehyde group(s) of the sugar compound is preferable.

Typical examples of the method for binding the enzyme to a sugar compound are illustrated, for example, as follows.

1) A carbodiimide method

2) A cyanogen bromide method

3) A periodate oxidation method

Binding of the sugar compound to the cholesterol esterase or the cholesterol oxidase can easily be conducted as follows.

One wt. part of the cholesterol esterase or the cholesterol oxidase and 0.1 to 100 wt parts of the sugar compound reactive with the enzyme as mentioned above are subjected to a reaction in a suitable solvent such as a buffer solution of pH 4 to 10, preferably 6 to 9 in the presence of, if necessary, a suitable amount of glutaraldehyde, a divalent cross-linking agent such as a dimaleimide compound including N,N'-phenylene dimaleimide, a carbodiimide reagent such as 1-ethyl-3-(3-dimethylaminopropyl) carbodiimide and dicyclohexyl carbodiimide, a condensation agent including a Woodward reagent such as N-ethyl-5-phenyl isoxazolium-3'-sulfonate, etc. at 1° to 50° C., preferably 4° to 40° C., for generally 30 minutes to 1 week, preferably 1 hour to 3 days, whereby the object cholesterol esterase or cholesterol oxidase bound to the sugar compound can be obtained.

Thus obtained modified cholesterol esterase or cholesterol oxidase is, if necessary, dialyzed into a suitable buffer solution and further the resultant may be condensed or freeze-dried after a suitable method.

In the modified cholesterol esterase or modified cholesterol oxidase obtained above, the weight ratio of the sugar compound to the enzyme is generally 100 to 1~1 to 5, preferably 20 to 1~1 to 1. The mole ratio of the sugar compound to the enzyme is generally 500 to 1~1 to 50, preferably 65 to 1~1 to 50. The ratio of the enzyme molecule to monosaccharide units of the sugar compound, for example, including glucose unit, mannose unit, fructose unit, galactose unit, fucose unit, etc., is generally 1 to 2800000~1 to 100, preferably 1 to 360000~1 to 100.

Additionally, upon the above modification reaction, stabilizer may be added to the reaction solution in order to prevent deactivation of the enzyme. The substance for this purpose is exemplified by all of those which have been known as a stabilizer, including protein such as bovine serum albumin, a polyol such as glycerol, a compound similar to the substrate to be used, co-enzyme, EDTA, a metal salt, etc.

As a buffer solution used in the reaction of the cholesterol esterase or the cholesterol oxidase with a sugar compound as a reaction solvent, use can be made of all buffer solutions which have been used in this field without any limitation, and preferable examples include those prepared from Good's buffer, phosphate buffer, borate buffer, etc., which has pH 4 to 10, preferably 6 to 9 and concentration of 5 mM to. 0.5M, preferably 10 mM to 100 mM.

The measuring an amount of LDL-cholesterol can be conducted according to a method which has been used in this field with the use of reagents which have generally been known in this field as reagents for measuring an amount of cholesterol, such as a reagent prepared by a method for preparation of a reagent containing a cholesterol oxidase, a cholesterol esterase, a peroxidase (POD), an oxidizable color forming agent, etc., using at least one, preferably two of the modified cholesterol esterase bound to the sugar compound (hereinafter abbreviated as the modified cholesterol esterase) and the modified cholesterol oxidase bound to the sugar compound (hereinafter abbreviated as the modified cholesterol oxidase) as prepared above.

The oxidizable color forming agent used in the reagent may be any of those which can react with hydrogen peroxide in the presence of a peroxidase to cause color formation, and is exemplified by a combination of a coupler such as 4-aminoantipyrine with a developer forming color by oxidative condensation with the coupler, including a combination of 4-aminoantipyrine with a phenol compound, a naphthol compound or an aniline compound, a combination of 3-methyl-2-benzothiazolinone hydrazone with an aniline compound, etc., and by a color former which forms color by itself by oxidation, including 2,2'-azinobis(3-ethylbenzothiazoline-6-sulfonic acid), a triphenylmethane compound, a diphenylamine derivative, a benzidine derivative, a triallyl imidazole derivative, a leuco methylene blue derivative, an o-phenylenediamine derivative, etc.

Specific examples of the phenol compound as the developer are phenol, p-chlorophenol, 2,4-dichlorophenol, etc., those of the naphthol compound are 1-naphthol, 1-naphthol-2-sulfonic acid, 1-naphthol-2-carboxylic acid, etc. and those of the aniline compound are N,N-diethylamine, N-ethyl-N-(β-hydroxyethyl)-m-toluidine, N-ethyl-N-(2-hydroxy-3-sulfopropyl)-3,5-dimethoxyaniline (DAOS), N-ethyl-N-(2-hydroxy-3-sulfopropyl)-3,5-dimethoxy-4-fluoroaniline (FDAOS), N-(2-hydroxy-3-sulfopropyl)-3,5-dimethoxyaniline (HDAOS), N-ethyl-N-(2-hydroxy-3-sulfopropyl)-m-toluidine (TOOS), N-ethyl-N-(3-methylphenyl)-N'-succinyl-ethylenediamine (EMSE), etc.

In case of using a combination of a coupler with a developer, an amount of the coupler to be used is not generalized because it is different according to the kind of the coupler and the developer to be combined, and it is usually selected from a range of generally 0.01 to 100 mM, preferably 0.1 to 10 mM, as concentration in the reaction solution upon measurement of cholesterol, and an amount in case of using 4-aminoantipyrine as the coupler is selected from a range of generally 0.01 to 50 mM, preferably 0.1 to 5 mM as concentration in the reaction solution upon measurement of cholesterol.

An amount of the developer to be used is not generalized because it is different according to the kind of the developer to be used and the coupler to be combined, and it is usually selected from a range of generally 0.01 to 50 mM, preferably 0.1 to 5 mM as concentration in the reaction solution upon measurement of cholesterol.

Specific examples of the triphenylmethane compund are leuco Malachite Green, bis(p-diethylaminophenyl)-2-sulfophenylmethane, bis(p-diethylaminophenyl)-3,4-disulfopropoxyphenylmethane disodium salt, etc., those of the diphenylamine derivatives are bis[4-di(2-butoxyethyl) amino-2-methylphenyl] amine, N,N-bis(4-diethylamino-2-methylphenyl)-N'-p-toluene sulfonyl urea, etc., those of leuco methylene blue derivative are 10-(carboxymethylaminocarbonyl)-3,7-bis(dimethylamino) phenothiazin sodium salt, 10-[3-(methoxycarbonylaminomethyl) phenylmethylaminocarbonyl]-3,7-bis(dimethylamino) phenothiazin, etc., those of the benzidine derivative are benzidine, o-tolidine, o-dianisidine, 3,3'-diaminobenzidine, 3,3',5,5'-tetraaminobenzidine, etc. and those of the triallyl imidazole are 2-(4-carboxyphneyl)-3-N-methylcarbamoyl-4,5-bis(4-diethylaminophenyl) imidazole, 2-(3-methoxy-4-diethylaminophenyl)-3-N-methylcarbamoyl-4,5-bis(2-methyl-4-diethylaminophenyl) imidazole, etc.

Amounts of each component in the reagent may be selected suitably from a range which has generally been used in measurement in this field. A buffer solution usable in the measurement of this invention may be any of one which has generally been used in this field and there is no specific limitation thereto. Concentration of the buffer solution is selected from a range generally of 2 mM to 1M, preferably 50 mM to 0.5M, though there is no specific limitation thereto, and a pH range may be any one so far as it is within a suitable range for enzymes, and is selected from a range preferably of 6 to 8, more preferably around 7.

An enzymatic activity of the enzyme after bound to the sugar compound is variable according to the origin of the enzyme, the kind of the sugar compound to be bound and the method for binding reaction, and thus an amount of the modified cholesterol esterase and the modified cholesterol oxidase to be used in the measuring method of the present invention is not limited specifically so far as it is within an amount capable of conducting the measurement, and it is generally selected from a range of 0.1 to 10 u/ml, preferably 0.5 to 2 u/ml as the concentration in the reaction solution in case of the modified cholesterol esterase and from a range of 0.1 to 10 u/ml, preferably 0.5 to 2 u/ml as the concentration in the reaction solution in case of the cholesterol oxidase. Those two enzymes may be incorporated in one and the same reagent or may be incorporated each in different reagents separately.

The reagent for measuring an amount of LDL-cholesterol of the present invention can be prepared as so-called one-reagent system or two- or more-reagent system, and there is no specific limitation thereto.

The reagent for measuring an amount of LDL-cholesterol by the method of the present invention may contain a surfactant. The surfactant used for this purpose includes any of nonionic, amphoteric, cationic and anionic ones without any specific limitation so far as it does not prevent the measurement of LDL-cholesterol, including specifically nonionic surfactant such as polyoxyethylene alkylphenyl ether (for example, polyoxyethylene isooctylphenyl ether, polyoxyethylene nonylphenyl ether, etc.), polyoxyethylene cetyl ether, polyoxyethylene oleyl ether, polyethyleneglycol monolaurate and polyoxyethylene lauryl ether; amphoteric surfactants such as stearyl betaine and 2-alkyl-N-carboxymethyl-N-hydroxyethyl imidazolinium betaine; cationic surfactants such as stearyl trimethylammonium chloride and alkylbenzyl dimethyl; anionic surfactants such as cholic acid, deoxycholic acid, and sodium polyoxyethylene alkylphenol ether sulfate, etc. as preferable embodiments.

The surfactant may be used alone or in combination of two or more thereof. An amount of the surfactant to be used is generally 0.001 to 1 (W/V%) in the reaction solution, though there is no specific limitation thereto.

The reagent for measuring an amount of LDL-cholesterol by the method of the present invention may contain an ionic compound. The ionic compound used for this purpose includes anionic compounds such as dextran sulfate, heparin, heparan sulfate, and phosphotungstic acid. They can be used in combination with a cation such as $Mg^{2+}$, $Mn^{2+}$ and $Ca^{2+}$ (or a metal salt generating the cation). An amount of the ionic compound to be used is not specifically limited and generally 0.01 to 10 (W/V%) in the reaction solution. In the reagent for measuring an amount of LDL-cholesterol by the method of the present invention, one or more of monoclonal antibodies or polyclonal antibodies may be incorporated in order to prevent the influence of cholesterols in lipoproteins other than LDL in the reaction.

The antibody used for this purpose includes anti-apoprotein. A antibody, anti-alpha-lipoprotein antibody, etc.

An amount of the antibody to be used is not specifically limited so far as it is not less than one preventing the influence of cholesterols in lipoproteins other than LDL, and generally 0.001 to 10 mgAb/ml, preferably 0.01 to 1 mgAb/ml as the final concentration in the reaction solution.

A method for measuring an amout of LDL-cholesterol of the present invention after so-called two-reagent system is conducted, for instance, as follows.

A living sample such as serum and plasma is mixed with a first reagent solution containing a coupler and a buffering agent and, if necessary, a metal salt, an anionic substance, an antibody, etc., followed by allowing a reaction to take place at 2° to 40° C. for 1 to 30 minutes, and then an absorbance (OD1) is measured, and then the resulting reaction solution is mixed with a second reagent solution containing the modified cholesterol esterase, the modified cholesterol oxidase, a developer, a peroxidase and if necessary a surfactant, followed by allowing a reaction to take place at 2° to 40° C. for 1 to 60 minutes and an absorbance (OD2) is measured. A value derived from the OD1 (for instance, value obtained by multiplying OD1 with a correction coefficient) is subtracted from the OD2 to give OD3. Thus obtained OD3 is applied to a calibration curve showing a relation between an amount of cholesterol and OD3 which is previously prepared by conducting the above process with the use of a standard solution containing a predetermined amount of cholesterol, whereby LDL-cholesterol amount in the living sample can be detected.

In the above mentioned measuring method, each of the coupler, the developer and the peroxidase may be incorporated in at least one of the first reagent and the second reagent. Preferably, one of the coupler and the developer is contained the first reagent and the other is contained in the second reagent.

The method for measuring an amount of LDL-cholesterol of the present invention can also be conducted by an one-reagent method as mentioned below.

For instance, a living sample such as serum and plasma is mixed with a reagent solution containing, for instance, the modified cholesterol esterase, the modified cholesterol oxidase, a peroxidase, an oxidizable color forming agent(or a coupler and a developer), a buffer agent, and if necessary, a metal salt, an anionic substance, an antibody, a surfactant, etc., followed by allowing a reaction to take place at 2° to 40° C. for 1 to 30 minutes, and an absorbance (OD1') is measured. The same procedure as above with the use of the same reagent as above except for using physiological saline in place of the living sample and a blank value (ODBl) is measured. Then the ODBl is subtracted from OD1' to give an absorbance (OD2'). This value is applied to a calibration curve showing a relation between an amount of cholesterol and OD2' which is previously prepared by conducting the above process with the use of a standard solution containing a predetermined amount of cholesterol, whereby LDL-cholesterol amount in the living sample can be detected.

The reagent for measuring an amount of LDL-cholesterol of the present invention is used for measuring an amount of LDL-cholesterol in a living sample such as serum and plasma, and the preferable embodiments of each ingredient, etc. and specific examples thereof are as mentioned above.

The characteristic feature of the present invention lies in that at least one of the cholesterol esterase and the cholesterol oxidase used in measuring an amount of LDL-cholesterol is a modified enzyme which is bound to a sugar compound, and it is quite unexpected that when LDL-cholesterol, VLDL-cholesterol and HDL-cholesterol are measured with the use of such modified enzymes, speeds of reactions with LDL-cholesterol, VLDL-cholesterol and HDL-cholesterol are clearly different from one another and thus LDL-cholesterol can specifically and separately be measured. Further, the modified enzymes of the present invention is found to be improved in their stability in an aqueous solution and thus their storage stability in solutions as compared with non-modified ones.

In the following, the present invention is further explained referring to reference examples and examples, but the present invention is not limited thereto by any means.

EXAMPLES

Activities of enzymes are measured by the following method in the following reference examples and examples.

a) Cholesterol esterase

Phosphate buffer solution (0.1M, pH 7.0, 3 ml) containing 0.4 mg of linolic acid cholesterol, 0.6 mg of 4-aminoantipyrine, 2 mg of phenol and 6 u of POD is charged in a cell of a spectrophotometer, and heated at 37 C for 5 minutes.

Ten microliter of a cholesterol esterase solution is added thereto so as to allow a reaction to take place. Change of absorbance (ΔA500) for 3 to 6 minutes at 500 nm wave length is measured and the activity of the choresterol esterase is obtained in accordance with the following equation 2;

$$u/ml = (\Delta A500 - \Delta A500 \text{ blank}) \times \frac{1}{3} \times 1/6.8 \times 3.01/0.01 \quad \text{(equation 2)}$$

b) Cholesterol oxidase

Phosphate buffer solution (0.1M, pH 7.0, 0.3 ml) containing 115 μg of cholesterol, 160 μg of 4-aminoantipyrine, 1.6 mg of phenol, 8.4 mg of Poly oxyethylene (10) pctylphenyl ether and 8.2 u of POD is charged in a cell of a spectrophotometer, and heated at 37° C. for 5 minutes.

One microliter of a cholesterol oxidase solution is added thereto so as to allow a reaction to take place. Change of absorbance (ΔA500) for 3 to 6 minutes at 500 nm wave length is measured and the activity of the cholesterol oxidase is obtained in accordance with the following equation 3:

$$u/ml = \Delta A500 \times \frac{1}{3} \times 1/6.8 \times 3.01/0.01 \quad \text{(equation 3)}$$

c) Peroxidase

The measurement of activities of a peroxidase is conducted after a method described in "Method of Enzymatic Analysis" 3rd ed., 1983, vol. II, 267.

Reference Example 1

One gram of dextran(M.W. 100000) was dissolved in 10 ml of water. One gram of sodium metaperiodide was added thereto, followed by allowing a reaction to take place at room temperature for 10 hours. The resultant was dialyzed with 0.2M N,N-bis(hydroxyethyl)-2-aminoethane sulfonic acid buffer solution (pH 7.0) (each 1 liter×3 times) to give 900 mg of activated dextran. Five mg of cholesterol esterase (originated from genus Pseudomonas, manufactured and sold by Amano Pharmaceutical Co., Ltd.) was added to 20 mM phosphate buffer solution (pH 7.0) containing 10 mg of the above obtained activated dextran, followed by allowing a reaction to take place at 25° C. for 1 day. After the reaction, the resultant was dialyzed with 20 mM phosphate buffer solution (pH 7.0) (each 1 liter×3 times) to give a modified cholesterol esterase.

The mole ratio of dextran to the cholesterol esterase in the modified cholesterol esterase: about 16 to 3.

The ratio of the cholesterol esterase molecule to glucose units of dextran in the modified cholesterol esterase about 1 to 300.

Reference Example 2

Five hundred milligrams of pullulan(M.W. 10000) was dissolved in 30 ml of 2M aqueous solution of sodium carbonate and 500 mg of cyanogen bromide dissolved in 1 ml of acetonitrile was added thereto, followed by allowing a reaction to take place for 5 minutes. After the reaction, the reaction solution was dialyzed with 0.1M aqueous solution of sodium bicarbonate (each 1 liter×3 times). Two grams of 5-aminocaproic acid was added to the obtained activated pullulan solution, followed by allowing a reaction to take place at 4° C. for 20 hours, and then the resultant was dialyzed with ion-exchanged water to give pullulan modified by 5-aminocaproic acid. Fifty millimole phosphate buffer solution (pH 7.0) containing 50 mg of the pullulan modified by 5-aminocaproic acid was mixed with 50 mg of cholesterol oxidase (originated from genus Nocardia, manufactured and sold by Boehringer Mannheim GmbH) dissolved in 5 ml of the same buffer solution, and 85 mg of water soluble carbodiimide was further added thereto, followed by allowing a reaction to take place at 15° C. for 18 hours. The resultant was dialyzed with 20 mM of phosphate buffer solution (pH 7.0) (each 1 liter×3 times) to give a modified cholesterol oxidase.

The mole ratio of dextran to the cholesterol oxidase in the modified cholesterol oxidase: about 6 to 10.

The ratio of the cholesterol oxidase molecule to glucose units of dextran in the modified cholesterol oxidase: about 1 to 340.

Example 1

[Reagent solution]

Fifty mM of 2-morpholinoethanesulfonic acid (MES) buffer solution (pH 7.0) containing 2 u/ml of the modified cholesterol esterase obtained in Reference Example 1, 2 u/ml of the modified cholesterol oxidase obtained in Reference Example 2, 3 mM of 4-aminoantipyrine, 0.6 mM of sodium N-ethyl-N-(2-hydroxy-3-sulfopropyl)-3,5-dimethoxyaniline (DAOS) and 5 u/ml of peroxidase was prepared as the reagent solution.

As a control, non-modified enzyme reagent solution was prepared by the same procedure as above except for using non-modified enzymes in place the modified enzymes.

[Sample]

Use were made, as samples, of 0.15M NaCl solution (containing 1M EDTA) containing predetermined amount of HDL, LDL or VLDL which was obtained by fractionating human serum by ultra-centrifugation method (F. J. Hatch, R. S. Lees, Adv. Lipid Res., vol. 6, 1, 1968).

[Measurement of cholesterol]

Three milliliters of the reagent solution was previously heated at 37° C. for 5 minutes and mixed with 10 μl of the sample, and a change of absorbance at 600 nm of the mixed solution is measured by a spectrophotometer.

[Result]

Figure 1:
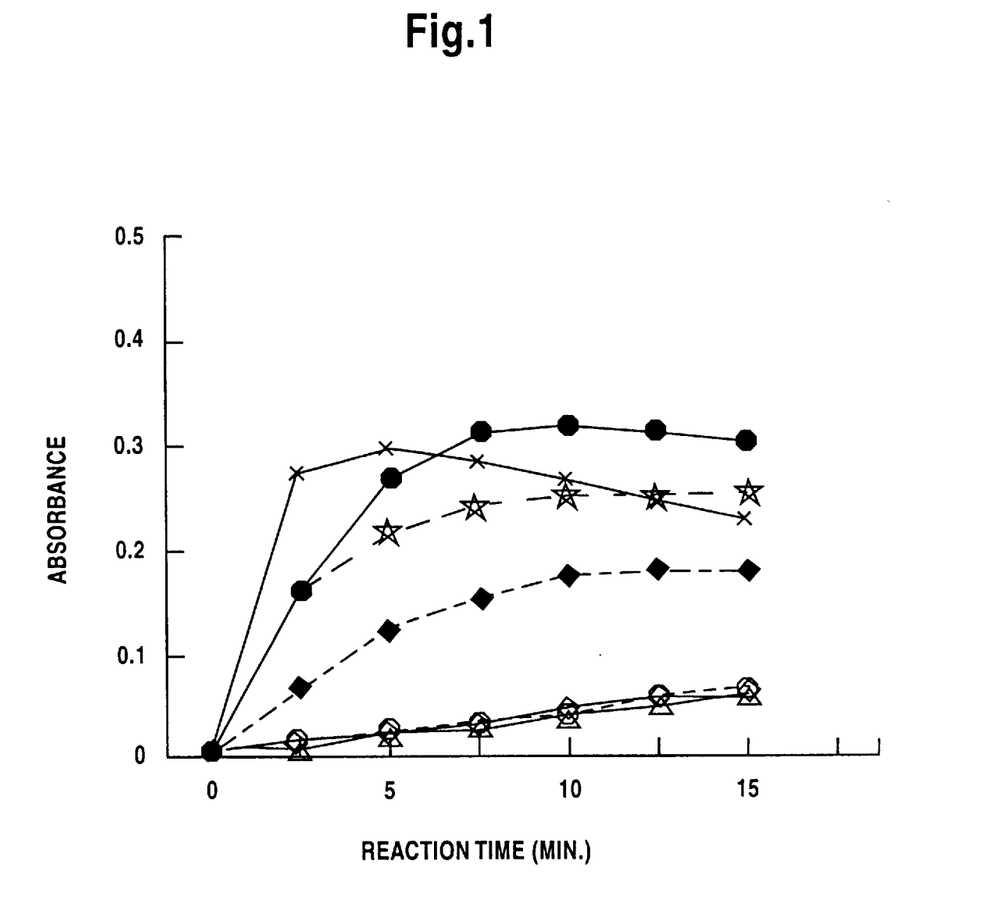
FIG. 1 shows reaction curves obtained in Example 1 where samples containing predetermined amount of low density lipoproteins (LDL) or high density lipoproteins (HDL) was reacted with the reagent of the present invention.

The result is shown in FIG. 1. In FIG. 1, -♦- shows the result in the sample 1 containing LDL (LDL concentration: 10 , μg/ml), -☆- shows the result in the sample 2 containing LDL (LDL concentration: 20 μg/ml), -●- shows the result in the sample 3 containing LDL (LDL concentration: 30 μg/ml), -◇- shows the result in the sample 4 containing HDL (HDL concentration: 5 μg/ml), -△- shows the result in the sample 5 containing HDL (HDL concentration: 10 μg/ml) and -○- shows the result in the sample 6 containing HDL (HDL concentration: 15 μg/ml), respectively.

As a control, the same measurement was conducted with the use of non-modified enzymes and the sample 6 containing HDL. The result is also shown in FIG. 1 (-×-).

It is understood from FIG. 1 that the absorbance is increased as the reaction proceeds and color is generated in accordance with the concentration of LDL in the sample in cases of the sample containing LDL, and that in cases of the samples containing HDL, on the other hand, almost no increase of absorbance is observed even after the reaction.

Upon measuring using non-modified enzymes as a control, it is understood that the absorbance is increased as the reaction proceeds and color is generated in accordance with the concentration of HDL in the samples (-×-in FIG. 1).

Figure 2:
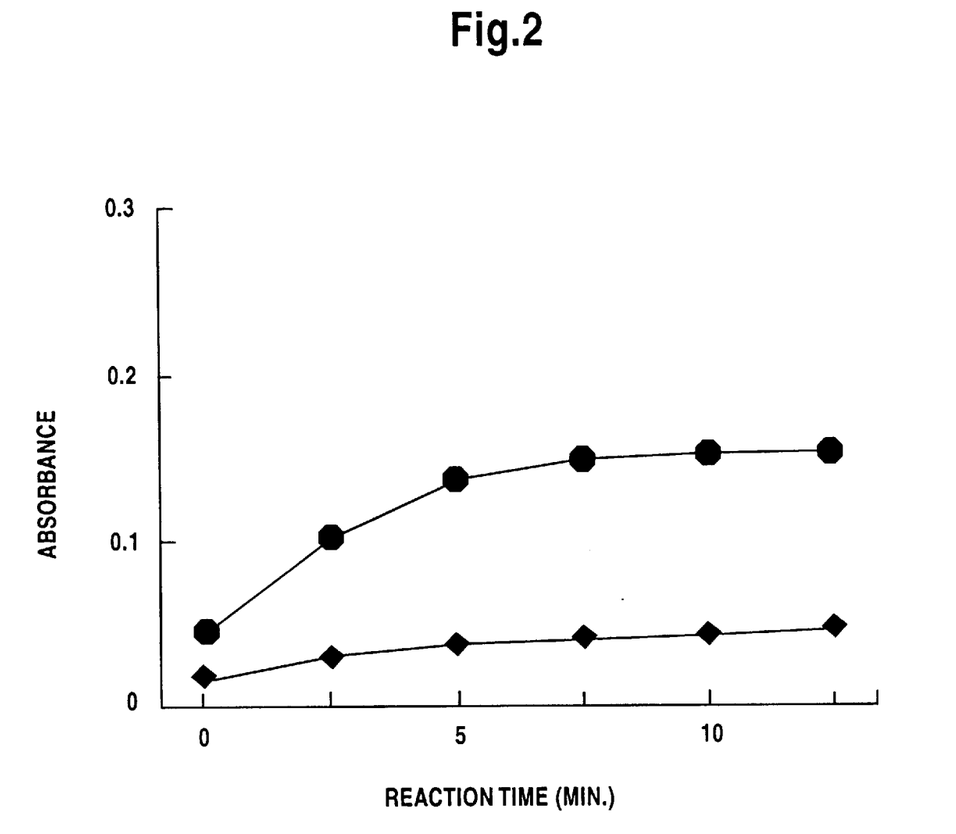
FIG. 2 shows reaction curves obtained in Example 1 where samples containing predetermined amount of very low density lipoproteins (VLDL) was reacted with the reagent of the present invention.

In FIG. 2, there are shown result of measurement in case of VLDL using non-modified enzymes and using the modified enzymes obtained in Reference Examples 1 and 2. In FIG. 2, -●- shows measurement result of the sample 7 containing VLDL (VLDL concentration: 10 μg/ml) using the reagent solution containing non-modified enzymes and -♦- shows that of the sample 7 containing VLDL (VLDL concentration: 10 μg/ml) using the reagent solution containing the modified enzymes.

From FIG. 1 and FIG. 2, it is understood that an amount of cholesterol in LDL can specifically be measured by the method of the present invention.

Figure 3:
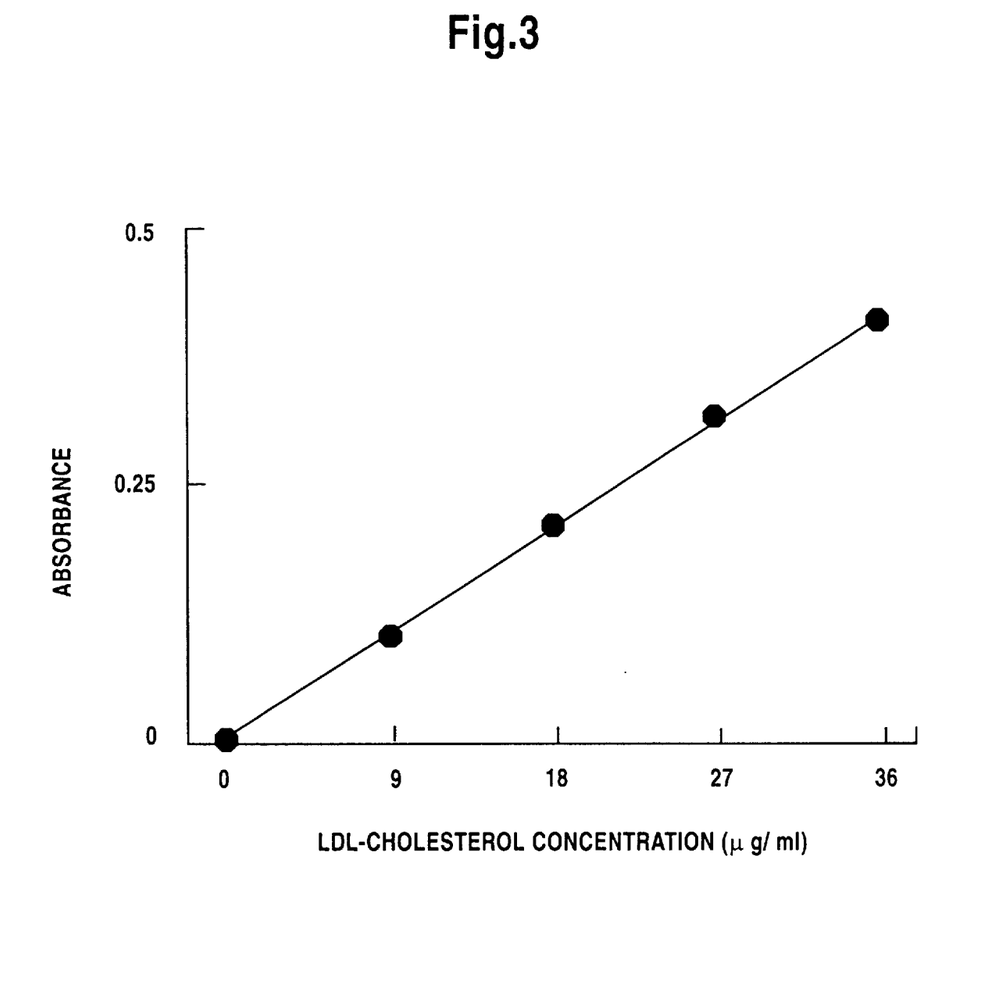
FIG. 3 shows a calibration curve of LDL-cholesterol by the method of the present invention, which was obtained in Example 1.
Figure 4:
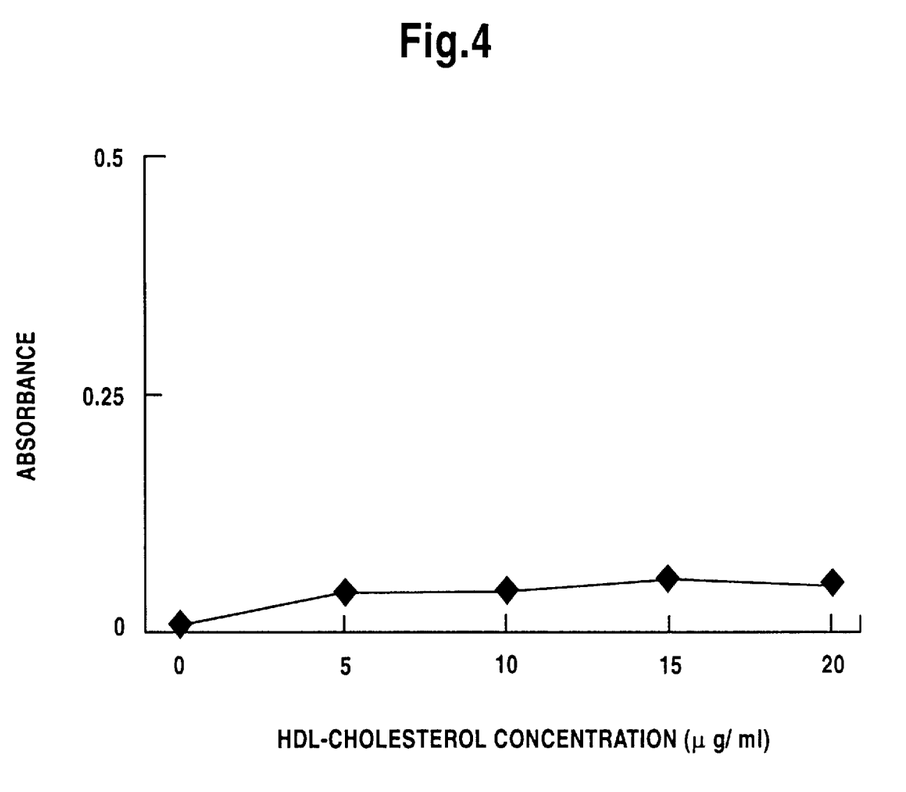
FIG. 4 shows a calibration curve of HDL-cholesterol by the method of the present invention, which was obtained in Example 1.

Further there are shown a calibration curve for LDL prepared by the same manner as above with the use of the above-mentioned reagents and a calibration curve for HDL prepared samely in FIG. 3 and FIG. 4, respectively.

From FIG. 3 and FIG. 4, it is understood that an amount of cholesterol in LDL can specifically and quantitatively be measured by the method of the present invention.

Example 2

The reagent solution containing the modified enzymes which was prepared in Example 1 and a reagent solution containing non-modified enzymes which was prepared in Example 1 were respectively stored in an incubator at 37° C. for 1 month, and then the remaining activities of each enzyme (relative activity when the enzymatic activity just after preparation is 100%) are measured.

The result is shown in Table 1.

TABLE 1

Remaining activity of each enzyme in reagent solutions (37° C. month)

| Enzyme | Remaining Activity (%) |
| --- | --- |
| modified cholesterol esterase | 64.1 |
| non-modified cholesterol esterase | 30.6 |
| modified cholesterol oxidase | 100 |
| non-modified cholesterol oxidase | 86.3 |

From the result in Table 1, it is understood that the modified enzymes of the present invention are remarkably improved in their stability in a solution as compared with non-modified enzymes, in other words, the reagents of the present invention have good storage stability in the state of solution.

As stated above, the present invention provides a method for measuring an amount of LDL-cholesterol in samples specifically and accurately and also a reagent used for the method, and by using the present invention, such effect can be attained that LDL-cholesterol can be measured directly using so far widely used automatic analyzer, which has been impossible in known measurement methods, and therefore the present invention can give great contribution in this kind of technical field.

What is claimed is:

1. A low density lipoprotein-cholesterol (LDL-cholesterol) specific reagent for directly measuring an amount of LDL-cholesterol by spectrophotographic absorbance which comprises:

cholesterol esterase and cholesterol oxidase, wherein at least one enzyme of the combination of enzymes is modified by having at least one amino group or at least one carboxyl group of said enzyme bound to a sugar compound and the resulting modified enzyme, consisting of either modified cholesterol esterase or modified cholesterol oxidase, does not react with high density lipoprotein-cholesterol but reacts only with LDL-cholesterol.

2. The reagent according to claim 1, wherein both the cholesterol esterase and the cholesterol oxidase are modified by being bound to a sugar compound.

3. The reagent according to claim 1, wherein the modified cholesterol esterase is one in which amino groups(s) of the cholesterol esterase is covalently bound to amino group(s), imino group(s), carboxyl group(s), aldehyde group(s), cyanuryl group(s) or epichlorohydryl group(s) of a sugar compound.

4. The reagent according to claim 1, wherein the modified cholesterol oxidase is one in which amino group(s) of the cholesterol oxidase is covalently bound to amino group(s), imino group(s), carboxyl groups(s), aldehyde group(s), cyanuryl group(s) or epichlorohydryl group(s) of a sugar compound.

5. The reagent according to claim 1, wherein the reagent further comprises a peroxidase and a color forming agent.

6. The reagent according to claim 5, wherein the color forming agent comprises a coupler and a developer.

7. The reagent according to claim 5, wherein the reagent further comprises a buffer and a surfactant.

8. A method for measuring an amount of LDL-cholesterol of a sample, which comprises the steps of:

mixing the sample with a first reagent solution containing a buffering agent to form a first reaction solution, measuring an absorbance (OD1) of the resulting first reaction solution, mixing the resulting solution with a second reagent solution containing a cholesterol esterase and a cholesterol oxidase to form a second reaction solution, measuring an absorbance (OD2) of the second resulting solution, subtracting a value obtained by multiplying OD1 with a correction coefficient from the OD2 to give OD3, and applying thus obtained OD3 to a calibration curve showing a relation between an amount of cholesterol and OD3 which is previously prepared by conducting the above process with the use of a standard solution containing a predetermined amount of cholesterol, wherein at least one of the cholesterol esterase and the cholesterol oxidase is modified in which the cholesterol esterase or the cholesterol oxidase is bound to a sugar compound, the resulting modified cholesterol esterase or cholesterol oxidase does not react with high density lipoprotein-cholesterol but reacts only with LDL-cholesterol, and each of a coupler, a developer and a peroxidase is incorporated in at least one of the reagent solutions.

9. The method according to claim 8, wherein one of the coupler and the developer is contained in the first reagent and the one not contained in the first reagent is contained in the second reagent.

10. The method according to claim 8, wherein both the cholesterol esterase and the cholesterol oxidase are modified by being bound to a sugar compound.

11. The method according to claim 8, wherein the modified cholesterol esterase is one in which amino group(s) of the cholesterol esterase is covalently bound to amino group (s), imino group(s), carboxyl group(s), aldehyde group(s), cyanuryl group(s) or epichlorohydryl group(s) of a sugar compound.

12. The method according to claim 8, wherein the modified cholesterol oxidase is one in which amino group(s) of the cholesterol oxidase is covalently bound to amino group (s), imino group(s), carboxyl group(s) aldehyde group(s), cyanuryl group(s) or epichlorohydryl group(s) of a sugar compound.

* * * * *